US00PP24262P2

(12) United States Plant Patent
Sakazaki

(10) Patent No.: US PP24,262 P2
(45) Date of Patent: Feb. 25, 2014

(54) ***FUCHSIA* PLANT NAMED 'USFUC0901'**

(50) Latin Name: *Fuchsia×hybrida*
Varietal Denomination: USFUC0901

(75) Inventor: Ushio Sakazaki, Shiga (JP)

(73) Assignee: Plant 21 LLC, Bonsall, CA (US)

( * ) Notice: Subject to any disclaimer, the term of this patent is extended or adjusted under 35 U.S.C. 154(b) by 6 days.

(21) Appl. No.: 13/507,527

(22) Filed: Jul. 5, 2012

(51) Int. Cl.
*A01H 5/00* (2006.01)

(52) U.S. Cl.
USPC ..... Plt./300

(58) Field of Classification Search
USPC ..... Plt./300
See application file for complete search history.

*Primary Examiner* — Kent L Bell
(74) *Attorney, Agent, or Firm* — C. A. Whealy

(57) ABSTRACT

A new and distinct cultivar of *Fuchsia* plant named 'USFUC0901', characterized by its upright and mounding to cascading plant habit; freely branching habit, dense and bushy plant form; vigorous growth habit; early and freely flowering habit; long flowering period; purple and red purple-colored flowers; and relative tolerance to high temperatures.

1 Drawing Sheet

Botanical designation: *Fuchsia×hybrida*.
Cultivar denomination: 'USFUC0901'.

BACKGROUND OF THE INVENTION

The present invention relates to a new and distinct cultivar of *Fuchsia* plant botanically known as *Fuchsia×hybrida* and hereinafter referred to by the name 'USFUC0901'.

The new *Fuchsia* plant is a product of a planned breeding program conducted by the Inventor in Higashiomi, Shiga, Japan. The objective of the breeding program is to create new mounding and freely branching *Fuchsia* cultivars with numerous attractive flowers and tolerance to high temperatures.

The new *Fuchsia* plant originated from a cross-pollination made by the Inventor on Jun. 12, 2008 in Higashiomi, Shiga, Japan of a proprietary selection of *Fuchsia×hybrida* identified as code number 08FJ03-01, not patented, as the female, or seed, parent with a proprietary selection of *Fuchsia×hybrida* identified as code number 08FJ07-02, not patented, as the male, or pollen, parent. The new *Fuchsia* plant was discovered and selected by the Inventor as a single flowering plant within the progeny of the stated cross-pollination in a controlled greenhouse environment in Higashiomi, Shiga, Japan on Sep. 14, 2009.

Asexual reproduction of the new *Fuchsia* plant by terminal cuttings in a controlled environment in Higashiomi, Shiga, Japan since Sep. 15, 2009 has shown that the unique features of this new *Fuchsia* plant are stable and reproduced true to type in successive generations.

SUMMARY OF THE INVENTION

Plants of the new *Fuchsia* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'USFUC0901'.

These characteristics in combination distinguish 'USFUC0901' as a new and distinct *Fuchsia* plant:

1. Upright and mounding to cascading plant habit.
2. Freely branching habit, dense and bushy plant form.
3. Vigorous growth habit.
4. Early and freely flowering habit.
5. Long flowering period.
6. Purple and red purple-colored flowers.
7. Relatively tolerant to high temperatures.

The new *Fuchsia* plant can be compared to plants of the female parent selection. Plants of the new *Fuchsia* differ primarily from plants of the female parent selection in the following characteristics:

1. Plants of the new *Fuchsia* are more mounding than and not as outwardly spreading as plants of the female parent selection.
2. Plants of the new *Fuchsia* flower earlier than plants of the female parent selection.
3. Plants of the new *Fuchsia* have larger flowers than plants of the female parent selection.

The new *Fuchsia* plant can be compared to plants of the male parent selection. Plants of the new *Fuchsia* differ primarily from plants of the male parent selection in the following characteristics:

1. Plants of the new *Petunia* are more vigorous than plants of the male parent selection.
2. Plants of the new *Petunia* are more mounding than and not as upright as plants of the male parent selection.
3. Plants of the new *Fuchsia* and the male parent selection differ in flower color as plants of the male parent selection have reddish pink-colored flowers.

Plants of the new *Fuchsia* can be compared to plants of 'Shabetty' disclosed in U.S. Plant Pat. No. 13,765. In side-by-side comparisons conducted in Bonsall, Calif., plants of the new *Fuchsia* and 'Shabetty' differed in the following characteristics:

1. Plants of the new *Fuchsia* were more vigorous than and not as compact as plants of 'Shabetty'.
2. Plants of the new *Fuchsia* and 'Shabetty' differed in flower color as plants of 'Shabetty' had red and white-colored flowers.

3. Plants of the new *Fuchsia* were more tolerant to high temperatures than plants of 'Shabetty'.

Plants of the new *Fuchsia* can also be compared to plants of 'Goetzimpro' disclosed in U.S. Plant Pat. No. 20,084. In side-by-side comparisons conducted in Bonsall, Calif., plants of the new *Fuchsia* and 'Goetzimpro' differed in the following characteristics:

1. Plants of the new *Fuchsia* were more vigorous than and not as compact as plants of 'Goetzimpro'.
2. Plants of the new *Fuchsia* and 'Goetzimpro' differed in flower color as plants of 'Goetzimpro' had light and dark pink-colored flowers.
3. Plants of the new *Fuchsia* were more tolerant to high temperatures than plants of 'Goetzimpro'.

BRIEF DESCRIPTION OF THE PHOTOGRAPHS

The accompanying colored photographs illustrate the overall appearance of the new *Fuchsia* showing the colors as true as it is reasonably possible to obtain in colored reproductions of this type. Colors in the photographs may differ slightly from the color values cited in the detailed botanical description which accurately describe the colors of the new *Fuchsia*.

The photograph at the bottom of the sheet comprises a side perspective view of a typical flowering plant of 'USFUC0901' grown in a container.

The photograph at the top of the sheet is a close-up view of a typical flowering plant of 'USFUC0901'.

DETAILED BOTANICAL DESCRIPTION

The aforementioned photographs and following observations, measurements and values describe plants grown during the spring in 20.3-cm containers in a polyethylene-covered greenhouse in Bonsall, Calif. and under cultural practices typically used in commercial *Fuchsia* production. During the production of the plants, day temperatures averaged 24° C., night temperatures averaged 17° C. and light levels averaged 4,000 foot-candle. Plants were pinched one time and were 17 weeks old when the photographs and the description were taken. In the following description, color references are made to The Royal Horticultural Society Colour Chart, 2007 Edition, except where general terms of ordinary dictionary significance are used.

Botanical classification: *Fuchsia×hybrida* 'USFUC0901'.

Parentage:

*Female, or seed, parent.*—Proprietary selection of *Fuchsia×hybrida* identified as code number 08FJ03-01, not patented.

*Male, or pollen, parent.*—Proprietary selection of *Fuchsia×hybrida* identified as code number 08FJ07-02, not patented.

Propagation:

*Type.*—By terminal cuttings.

*Time to initiate roots, summer.*—About four days at temperatures ranging from 17° C. to 29° C.

*Time to initiate roots, winter.*—About six days at temperatures ranging from 17° C. to 21° C.

*Time to produce a rooted plant, summer.*—About 23 days at temperatures ranging from 17° C. to 29° C.

*Time to produce a rooted plant, winter.*—About 25 days at temperatures ranging from 17° C. to 21° C.

*Root description.*—Medium in thickness, fibrous; white in color.

*Rooting habit.*—Freely branching; medium density.

Plant description:

*Plant and growth habit.*—Upright and mounding to cascading growth habit; freely branching habit with about 20 primary lateral branches each with multiple secondary and tertiary lateral branches developing per plant; pinching enhances lateral branch development; dense and bushy plant form; vigorous growth habit.

*Plant height.*—About 18 cm.

*Plant diameter.*—About 63 cm.

Lateral branch description:

*Length.*—About 28 cm.

*Diameter.*—About 3 mm.

*Internode length.*—About 2.7 cm.

*Strength.*—Strong.

*Aspect.*—Initially upright then outwardly arching to drooping.

*Texture.*—Sparsely pubescent; with development, smooth, woody.

*Color.*—Close to 195A tinted with close to 183D; woody stems, close to 199A.

Foliage description:

*Arrangement.*—Opposite, simple.

*Length.*—About 4.3 cm.

*Width.*—About 1.6 cm.

*Shape.*—Elliptic to slightly lanceolate.

*Apex.*—Acute to slightly apiculate.

*Base.*—Attenuate with obtuse tendencies.

*Margin.*—Minutely serrate.

*Texture, upper and lower surfaces.*—Smooth, glabrous.

*Venation pattern.*—Pinnate; arcuate.

*Color.*—Developing leaves, upper surface: Close to N137A. Developing leaves, lower surface: Close to 146A. Fully expanded leaves, upper surface: Close to 147A; venation, close to 187B. Fully expanded leaves, lower surface: Close to 147B; venation, close to 183C.

*Petiole.*—Length: About 1.3 cm. Diameter: About 1 mm. Texture, upper and lower surfaces: Pubescent. Color, upper surface: Close to 183C. Color, lower surface: Close to 183D.

Flower description:

*Flower arrangement and habit.*—Single axillary flowers; flowers radially symmetrical and pendulous; freely flowering habit, typically two flowers develop per leaf axil; about 1,800 flowers per plant.

*Fragrance.*—None detected.

*Natural flowering season.*—Long flowering period; plants flower continuously from spring until frost in California.

*Flower longevity.*—Flowers last about three to four days on the plant; flowers not persistent.

*Flower diameter.*—About 5.3 cm.

*Flower height (depth).*—About 5.5 cm.

*Corolla diameter.*—About 1 cm.

*Flower buds.*—Shape: Oblanceolate. Length: About 3.7 cm. Diameter: About 8 mm. Color: Close to N57A to N57C.

*Corolla.*—Quantity of petals and arrangement: Typically four petals arranged in a single whorl; petals imbricate. Petal length: About 2.3 cm. Petal width: About 1.5 cm. Petal shape: Obovate. Petal apex: Rounded. Petal base: Attenuate. Petal margin: Entire. Petal texture, upper and lower surfaces: Smooth, glabrous; velvety. Petal color: When opening, inner surface: Close to N81A. When opening, outer surface: Close to 83B. Fully opened, inner surface: Close to 77A; towards the base, close to N66B; color becomes closer to 71A with development. Fully opened, outer surface: Close to 77A; towards the base, close to 67B; color becomes closer to slightly darker than 72A with development.

*Calyx.*—Quantity of sepals and arrangement: Typically four sepals arranged in a single whorl and fused at the base; calyx star-shaped. Sepal length: About 2.7 cm. Sepal width: About 5 mm. Sepal shape: Gladiate; reflexed. Sepal apex: Acute. Sepal margin: Entire. Sepal texture, upper and lower surfaces: Smooth, glabrous; velvety. Sepal color: When opening and fully opened, upper surface: Close to 58B. When opening and fully opened, lower surface: Close to 54A.

*Peduncles.*—Length: About 2.9 cm. Diameter: About 1 mm. Aspect: About 45° to 55° from the stem axis. Strength: Strong. Texture: Smooth, glabrous. Color: Close to 146C.

*Reproductive organs.*—Stamens: Quantity: Eight per flower. Filament length: About 1.8 cm. Filament color: Close to 53C. Anther shape: Oblong. Anther size: About 3.5 mm. Anther color: Close to 185A. Pollen amount: Moderate. Pollen color: Close to 199C. Pistils: Quantity: One per flower. Pistil length: About 4.3 cm. Style length: About 3.8 cm. Style color: Close to 53D. Stigma shape: Globose. Stigma color: Close to 47A. Ovary color: Close to 137B.

*Seeds and fruits.*—Seed and fruit development have not been observed on plants of the new *Fuchsia.*

Temperature tolerance: Plants of the new *Fuchsia* have relatively good low and high temperature tolerance and have been observed to tolerate temperatures ranging from about 2° C. to about 38° C.

Pathogen & pest resistance: Plants of the new *Fuchsia* have not been observed to be resistant to pests and pathogens common to *Fuchsia* plants.

It is claimed:

1. A new and distinct *Fuchsia* plant named 'USFUC0901' as illustrated and described.

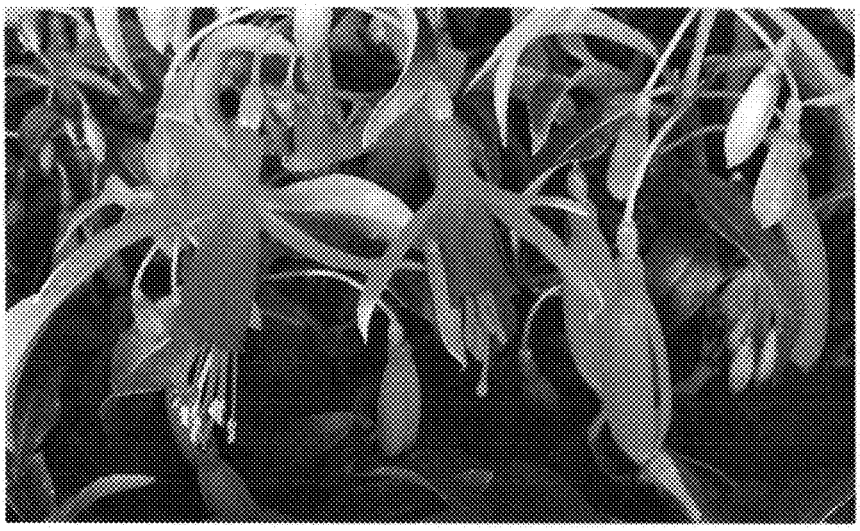
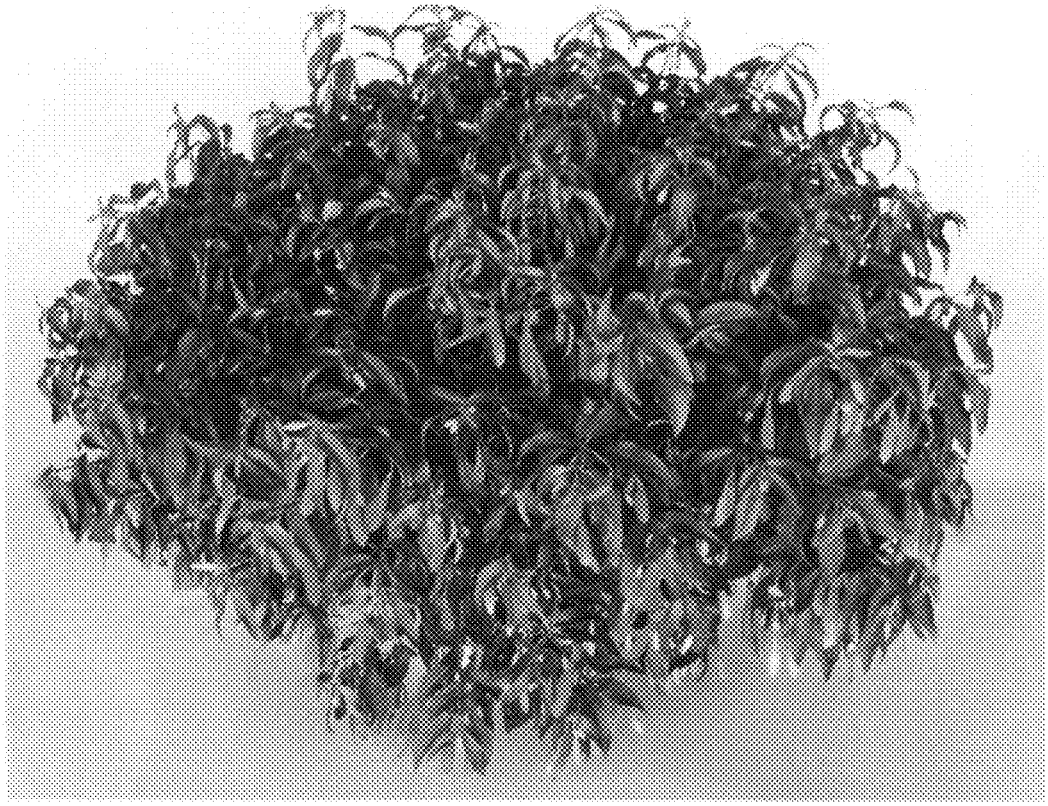

* * * * *